United States Patent [19]

Daviduk et al.

[11] Patent Number: 4,544,788
[45] Date of Patent: Oct. 1, 1985

[54] CONTROL SYSTEM FOR CATALYTIC CONVERSION OF OLEFINS TO HEAVIER HYDROCARBONS

[75] Inventors: Nicholas Daviduk, Pennington; Hartley Owen, Bell Mead; Bernard S. Wright, East Windsor, all of N.J.

[73] Assignee: Mobil Oil Corporation, New York, N.Y.

[21] Appl. No.: 686,963

[22] Filed: Dec. 28, 1984

[51] Int. Cl.[4] .......................... C07C 3/02; C07C 3/20; C07C 3/10

[52] U.S. Cl. .............................. 585/501; 208/DIG. 1; 422/106; 422/131; 422/190; 585/401; 585/403; 585/408; 585/469; 585/701; 585/415; 585/533

[58] Field of Search ................. 208/DIG. 1; 422/190, 422/191, 194, 206, 207, 198, 211, 106, 112, 105, 131; 585/408, 401, 402, 403, 469, 501, 701, 415, 533

[56] References Cited

U.S. PATENT DOCUMENTS

| | | | |
|---|---|---|---|
| 3,725,653 | 4/1973 | Carr et al. ..................... | 208/DIG. 1 |
| 3,829,376 | 8/1974 | Hopkins et al. .............. | 208/DIG. 1 |
| 4,132,529 | 1/1979 | Schwimmer .................. | 208/DIG. 1 |
| 4,433,185 | 2/1984 | Tabak ............................ | 585/312 |
| 4,444,988 | 4/1984 | Capsuto et al. ............... | 585/415 |
| 4,450,311 | 5/1984 | Wright et al. ................. | 585/413 |
| 4,456,779 | 6/1984 | Owen et al. .................. | 585/415 |
| 4,497,968 | 2/1985 | Wright et al. ................. | 585/304 |

OTHER PUBLICATIONS

Considine, "Process Instruments and Controls Handbook", 2nd Ed. (McGraw-Hill), 1974.

Primary Examiner—D. E. Gantz
Assistant Examiner—A. Pal
Attorney, Agent, or Firm—A. J. McKillop; M. G. Gilman; L. G. Wise

[57] ABSTRACT

A control system is provided for an olefins upgrading plant wherein catalytic reactor effluent is separated to recover heavy, intermediate and light hydrocarbon streams. An improved liquid recycle system includes a level control technique for diverting a portion of a separator overhead vapor stream. Recycle flow rate may be determined by reactor temperature differential in a series of adiabatic catalytic reactors.

7 Claims, 3 Drawing Figures

CONTROL SYSTEM FOR CATALYTIC CONVERSION OF OLEFINS TO HEAVIER HYDROCARBONS

FIELD OF INVENTION

This invention relates to a continuous technique for the manufacture of heavy hydrocarbons, especially distillate range fuels. In particular it provides a control system for operating an MOGD type plant wherein an oligomerization catalyst is employed for converting olefinic feedstocks at elevated temperature and pressure.

BACKGROUND OF THE INVENTION

Upgrading olefins to make gasoline and/or distillate products is disclosed in U.S. Pat. Nos. 3,960,978 and 4,021,502 (Givens, Plank and Rosinski) wherein gaseous olefins in the range of ethylene to pentene, either alone or in admixture with paraffins are converted into an olefinic gasoline blending stock by contacting the olefins with a catalyst bed made up of a ZSM-5 type zeolite. In U.S. Pat. No. 4,227,992 Garwood and Lee disclose the operating conditions for the Mobil Olefin to Gasoline/Distillate (MOGD) process for selective conversion of $C_3+$ olefins to mainly aliphatic hydrocarbons. In a related manner, U.S. Pat. Nos. 4,150,062 and 4,211,640 (Garwood et al) discloses a process for converting olefins to gasoline components. Typically, the process recycles gas or liquid hydrocarbons from a high-temperature, high-pressure separator downstream of the catalyst bed back into the reaction zone where additional olefins are converted to gasoline and distillate products. If the reaction of the olefins in converting them to distillate and gasoline is allowed to progress in the catalyst stream without any measures taken to prevent the accumulation of heat, the reaction becomes so exothermically accelerated as to result in high temperatures and the production of undesired products.

In the process for catalytic conversion of olefins to heavier hydrocarbons by catalytic oligomerization/-polymerization using a medium pore shape selective acid crystalline zeolite, such as ZSM-5 type catalyst, process conditions can be varied to favor the formation of either gasoline or distillate range products. At moderate temperature and relatively high pressure, the conversion conditions favor aliphatic distillate range product having an initial point of at least 165° C. (330° F.). Lower olefinic feedstocks containing $C_2$-$C_8$ alkenes may be converted; however, the distillate mode conditions do not convert a major fraction of ethylene. One source of olefinic feedstocks of interest for conversion to heavier fuel products is the intermediate olefin-rich light oil obtained from Fischer-Tropsch conversion of synthesis gas.

It is a main object of this invention to provide a continuous system for upgrading lower and intermediate olefins, such as Synthol light oil, to a valuable heavy distillate fuel product. Control apparatus and processes for operating a production plant are provided in a unique system for monitoring process conditions and effecting changes in recycle flow ratio and reactor temperature.

An improved continuous catalytic conversion system has been devised for upgrading olefinic feedstock in contact with a bed of oligomerization catalyst at elevated temperature and pressure in an enclosed reaction system to produce an effluent stream comprising a mixture of heavy hydrocarbons and lighter hydrocarbons including means for flashing and phase separation of a liquid product stream rich in heavy hydrocarbons and a vapor stream rich in lighter hydrocarbons. A recycle control system is provided, including condenser means for condensing a major amount of said flashed vapor stream rich in lighter hydrocarbons, a surge drum for receiving the condensed stream, fluid handling means operatively connected between the surge drum and reactor for repressurizing and combining a predetermined amount of recycled hydrocarbons with olefinic feedstock, and valve means for withdrawing a vapor slipstream between said flashing means and the condenser means to divert flashed vapors. Measurement and process control functions are provided by means for detecting liquid level of condensed hydrocarbons in said surge drum and generating a signal representative of the liquid level; and control means responsive to the level signal and operatively connected with the slipstream diverting valve means, whereby vapor slipstream flow is increased with increased surge drum liquid level above a predetermined level.

It is a further object of this invention to provide a novel technique for controlling and varying the composition and weight ratio of the gasoline and distillate produced. It allows a weight ratio change in product yields without changing the feed composition or rate. Also, if distillate is to be used for diesel fuel, a distillate of increased specific gravity may be produced to meet diesel fuel specifications, and to enhance its lubricating properties.

These and other objects and features of the invention will be understood from the following detailed description and drawings.

THE DRAWINGS

DESCRIPTION OF THE PREFERRED EMBODIMENTS

The oligomerization/polymerization catalysts preferred for use herein include the crystalline aluminosilicate zeolites having a silica to alumina ratio of at least 12, a constraint index of about 1 to 12 and acid cracking activity of about 160–200. Representative of the ZSM-5 type zeolites are ZSM-5, ZSM-11, ZSM-12, ZSM-23, ZSM-35 and ZSM-38. ZSM-5 is disclosed and claimed in U.S. Pat. No. 3,702,886 and U.S. Pat. No. Re. 29,948; ZSM-11 is disclosed and claimed in U.S. Pat. No. 3,709,979. Also, see U.S. Pat. No. 3,832,449 for ZSM-12; U.S. Pat. No. 4,076,842 for ZSM-23; U.S. Pat. No. 4,016,245 for ZSM-35 and U.S. Pat. No. 4,046,839 for ZSM-38. The disclosures of these patents are incorporated herein by reference. A suitable shape selective medium pore catalyst for fixed bed is HZSM-5 zeolite with alumina binder in the form of cylindrical extrudates of about 1–5 mm. Other pentasil catalysts which may be used in one or more reactor stages include a variety of medium pore (~5 to 9A) siliceous materials such as borosilicates, ferrosilicates, and/or aluminosilicates disclosed in U.S. Pat. Nos. 4,414,423, 4,417,086, 4,417,087 and 4,417,088, incorporated herein by reference.

Figure 1:
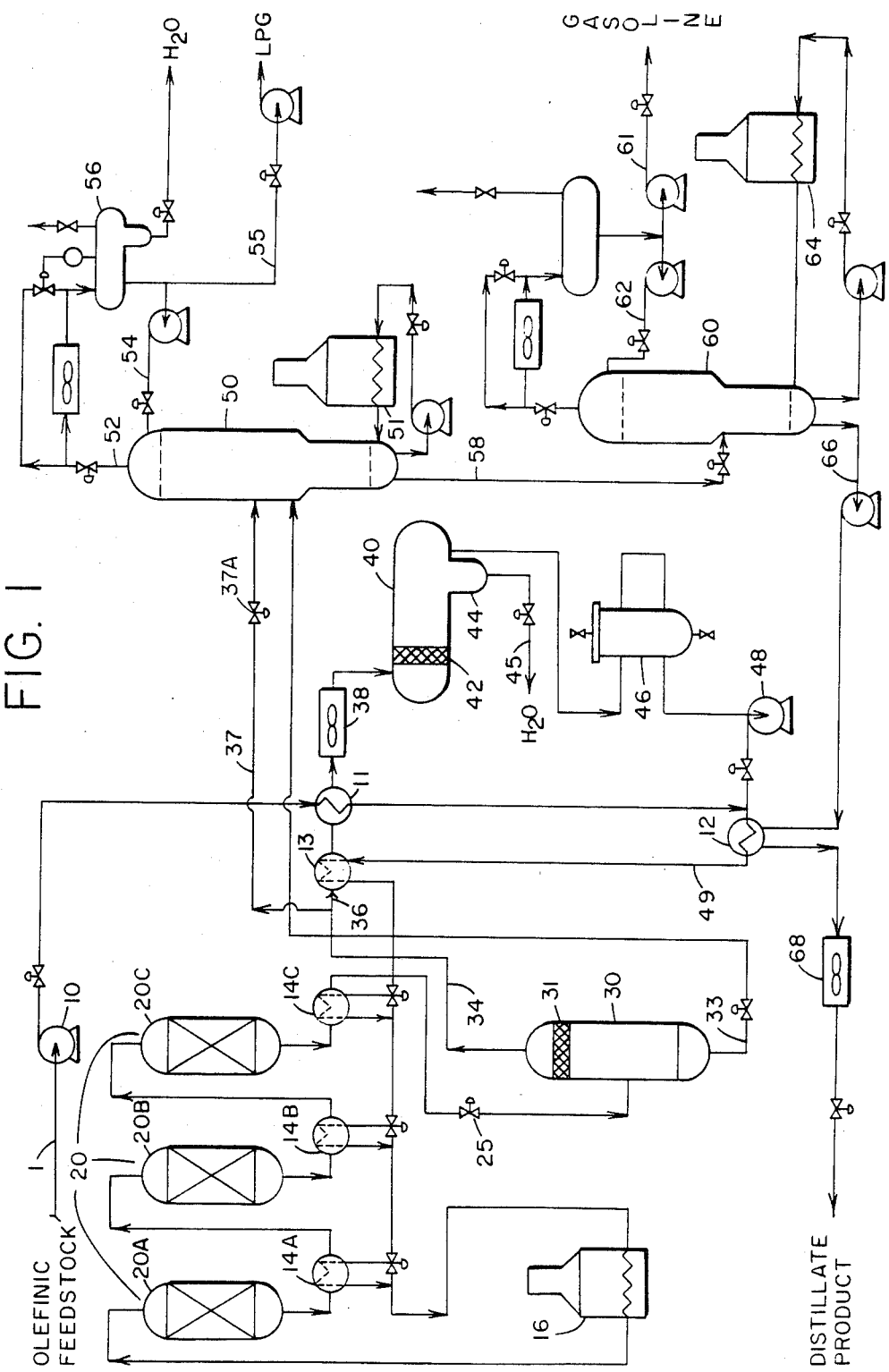
FIG. 1 is a process flow sheet showing the major unit operations and process streams.

The flowsheet diagram of FIG. 1 shows the relationship of the inventive process to the preceding syngas conversion and prefractionation unit operations, depicting the further conversion of the $C_5$-$C_6$ rich olefinic intermediate, phase separation and recycle. Heavy hydrocarbons are recovered by fractionation and sent to a conventional hydrotreating unit for product finishing.

The present invention provides a continuous economic process for converting lower olefins to heavier hydrocarbons. It is an object of the present invention to separate olefinic gasoline from reactor effluent in an efficient manner to provide a recycle stream rich in $C_5$ to $C_9$ hydrocarbons and having only minor amounts of $C_4^-$ compounds or distillate range product. The gasoline recycle stream is obtained by a phase separation technique wherein the reactor effluent stream is cooled to condense heavy hydrocarbons, especially distillate materials, which are recovered in a liquid stream. These aspects are shown in greater detail in FIG. 1 and in the following description.

GENERAL PROCESS DESCRIPTION

The olefinic feedstock supply 1 is normally liquid and can be brought to process pressure by means of pump 10 and preheated by passing sequentially through a series of heat exhange means 11, 12, 13 and reactant effluent exchangers 14C, B, A, and furnace 16 prior to entering the catalytic reactor system 20.

A typical distillate mode first stage reactor system 20 is shown. A multi-reactor system is employed with inter-zone cooling, whereby the reaction exotherm can be carefully controlled to prevent excessive temperature above the normal moderate range of about 230° to 325° C. (450°–620° F.). While process pressure may be maintained over a wide range, usually from about 2800 to over 10,000 kPa (400–1500 psia), the preferred pressure is about 4000 to 7000 kPa (600 to 1000 psia). The feedstock is heated to reaction temperature and carried sequentially through a series of zeolite beds 20A, B, C wherein at least a portion of the olefin content is converted to heavier distillate constituents. Advantageously, the maximum temperature differential across only one reactor is about 30° C. ($\Delta T \sim 50°$ F.) and the space velocity (LHSV based on olefin feed) is about 0.5 to 1.5. In addition, to maximizing gasoline and distillate yields, the temperature rise across the reactor beds is controlled by the amount of recycle mixed with the fresh olefinic feed. Limiting the temperature rise across one or more of the reactor beds minimizes the amount of undesirable light hydrocarbons (i.e., $C_1$ to $C_4$) produced. The heat exchangers 14A and 14B provide inter-reactor cooling and 14C reduces the effluent to flashing temperature. Control valve 25, operatively connected between the reactor section 20 and phase separator unit 30 provides means for reducing the process pressure, thereby vaporizing volatile components of the effluent stream, such as unreacted lighter hydrocarbons (e.g. $C_5$-$C_6$ alkenes) and water. The separator may be a vertical cylindrical vessel having a hooded tangential inlet to effect separation of the flashed effluent mixture. A demister pad 31 prevents substantial liquid entrainment and a major amount of the overhead vapor is withdrawn through conduits 34, 36, cooled indirectly by total reactor feed in exchanger 13 and incoming feedstock in exchanger 11 and passed through air cooler 38 to condense the lighter hydrocarbons in the separator vapor phase along with byproduct water from oxygenate conversion. Surge tank 40 includes a coalescer zone 42 to separate water, which is withdrawn from the system through boot 44 and outlet 45. Condensed vapor provides essentially all of the liquid olefinic recycle stream and is passed from the surge tank 40 through filter means 46 and pressurized by pump means 48 prior to combining with feedstock in conduit 49.

The temperature and pressure at which separator 30 operates determines the composition of the recycle stream. A light molecular weight overhead vapor stream is obtained by operating the separator at a relatively low temperature and high pressure to reduce the amount of flash. A light overhead stream, which becomes the recycle stream, results in producing more gasoline and less distillate boiling range components than a heavier component overhead stream. When a heavier diesel fuel is the desired product, the temperature of the separator is increased and/or the pressure is decreased to provide a recycle stream of increased molecular weight. The separator overhead stream is split into 2 streams in a weight ratio varying from about 1:1 to 20:1, with a ratio of 10–15:1 being preferred. The larger stream is cooled and condensed and enters surge drum 40.

Liquid hydrocarbons rich in distillate are recovered from phase separator 30 at flashing pressure, preferably about 1100 to 1500 kPa (160 to 220 psia) and passed via conduit 33 to debutanizer fractionation tower 50 at a lower stage therein where the heavy liquid contacts rising vapor from reboiler section 51 to vaporize dissolved lighter hydrocarbons, especially $C_4^-$ hydrocarbons present in the feedstock or generated during conversion. The debutanizer overhead stream 52 may be cooled to produce reflux 54 and recovered as LPG byproduct through conduit 55 from accumulator 56.

Advantageously, the technique to control product composition is based on varying the composition and ratio of a recycle stream flow rate to fresh olefinic feedstream flow rate along with varying reactor pressure. The desired recycle stream is obtained by flashing the effluent from the MOGD conversion reactors under controlled temperature and pressure conditions.

The amount of recycle can be varied according to need. During steady state operation at design conditions, a minor amount (e.g. 7–8%) of separator overhead vapor from line 34 is taken as a slipstream through conduit 37 via control valve 37A and sent directly to the debutanizer tower 50 at an intermediate stage thereof. This vapor slipstream is important to purge the process loop of accumulated light vapor components. By opening and closing diverter control valve 37A, the amount of vapor passing through cooler 38 and surge tank 40 is controlled, and thereby the liquid level of condensed hydrocarbons available for recycle is changed. The control system for this function is described hereafter in detail.

Light hydrocarbons and byproduct water are withdrawn with the tower overhead stream 52 and heavier hydrocarbons containing gasoline and distillate range hydrocarbons are sent along with the debutanizer bottoms stream 58 to product splitter 60 where the heavier hydrocarbons are fractionated to provide a condensed gasoline product 61 and condensed reflux 62. Splitter tower 60 has a furnace fired reboiler section 64 and the refined heavy distillate product is recovered through conduit 66, and cooled by exchanging against both the incoming feedstock and the recycle in exchanger 12 and then further cooled in cooler 68. Advantageously, the distillate-rich liquid phase is fractionated to provide a major product stream consisting essentially of 154° C.+ aliphatic hydrocarbons comprising a major amount of $C_{10}$–$C_{20}$ aliphatic hydrocarbons. This product may then be hydrotreated in a separate process step (not shown) to provide a heavy distillate product having a viscosity of at least about 1.8 centistokes at 40° C. Details of a mild hydrogenation treatment may be obtained from U.S. Pat. No. 4,211,640, incorporated by reference, typically using Co or Ni with W/Mo and/or noble metals.

In order to obtain heavy distillate product having a relatively high viscosity, higher reaction pressures are employed. For instance, if a 3 centistoke at 40° C. fuel product is required, a process pressure of at least 5500 kPa (800 psia) is suggested.

There are several advantages to the process design. The heavier recycle consists essentially of $C_5$+ hydrocarbons, with minor amounts of $C_4$- components. This recycle material has a relatively high heat capacity and provides a good heat sink without diminishing feedstock olefin partial pressure and thereby maintaining a high olefin partial pressure at reactor inlet. The liquid recycle is economically repressurized by pumping, which requires modest power consumption. The debutanizer is operable at about 1000 kPa (150 psi) to condense all overhead without refrigeration, thus providing energy efficiency in obtaining the LPG byproduct. The product splitter tower can be operated at atmospheric pressure, thus holding the bottoms temperature to less than 273° C. (525° F.) to provide raw distillate product stability.

A typical distillate mode oligomerization operation may be conducted over a fixed bed of HZSM-5/alumina extrudate catalyst using the techniques described in U.S. Pat. No. 4,456,779 (Owen et al) and U.S. Pat. No. 4,433,185 (Tabak), incorporated herein by reference. Reactor sequencing and catalyst regeneration are known in the art. Feedstock may be derived from synthesis gas conversion product made according to a commercial Fischer-Tropsch process, for instance, as disclosed in U.S. Pat. No. 4,111,792. Typically, such materials have an oxygenated hydrocarbon content of at least about 2 wt percent. A typical $C_5$–$C_6$ (75 mole percent) olefin fractionation cut containing coproduced alcohol, ethers, aldehyde, and/or ketone oxygenates can be water washed to remove excess oxygenates and reduce their amount to an acceptable level. Typical feedstock and product specifications are disclosed in copending U.S. patent application Ser. No. 600,642 filed Apr. 16, 1984, incorporated herein by reference.

Process Control

The following description of the preferred control techniques is intended to be implemented by state-of-the-art devices, including a dedicated digital process computer or the like. The protocol for maintaining the process conditions at the desired optimum during plant startup, steady state operation, reactor changeover and shutdown should be carefully delineated. A typical protocol provides the following function: select product quality and capacity; input reactor conditions; feed and recycle rates; establish unit operation limits; sequence reactors and control regeneration loop; monitor process upset and reset control functions. Product streams are controlled to obtain the desired light, middle and heavy hydrocarbon products; especially for acceptable gasoline, distillate and lubricant range aliphatics. Various process upsets may be accomodated, such as changes in feedstock composition. Greater exothermic heat release can be realized by increased propylene in the feedstock or by increased catalyst activity due to end of cycle reactor changeover.

Figure 2:
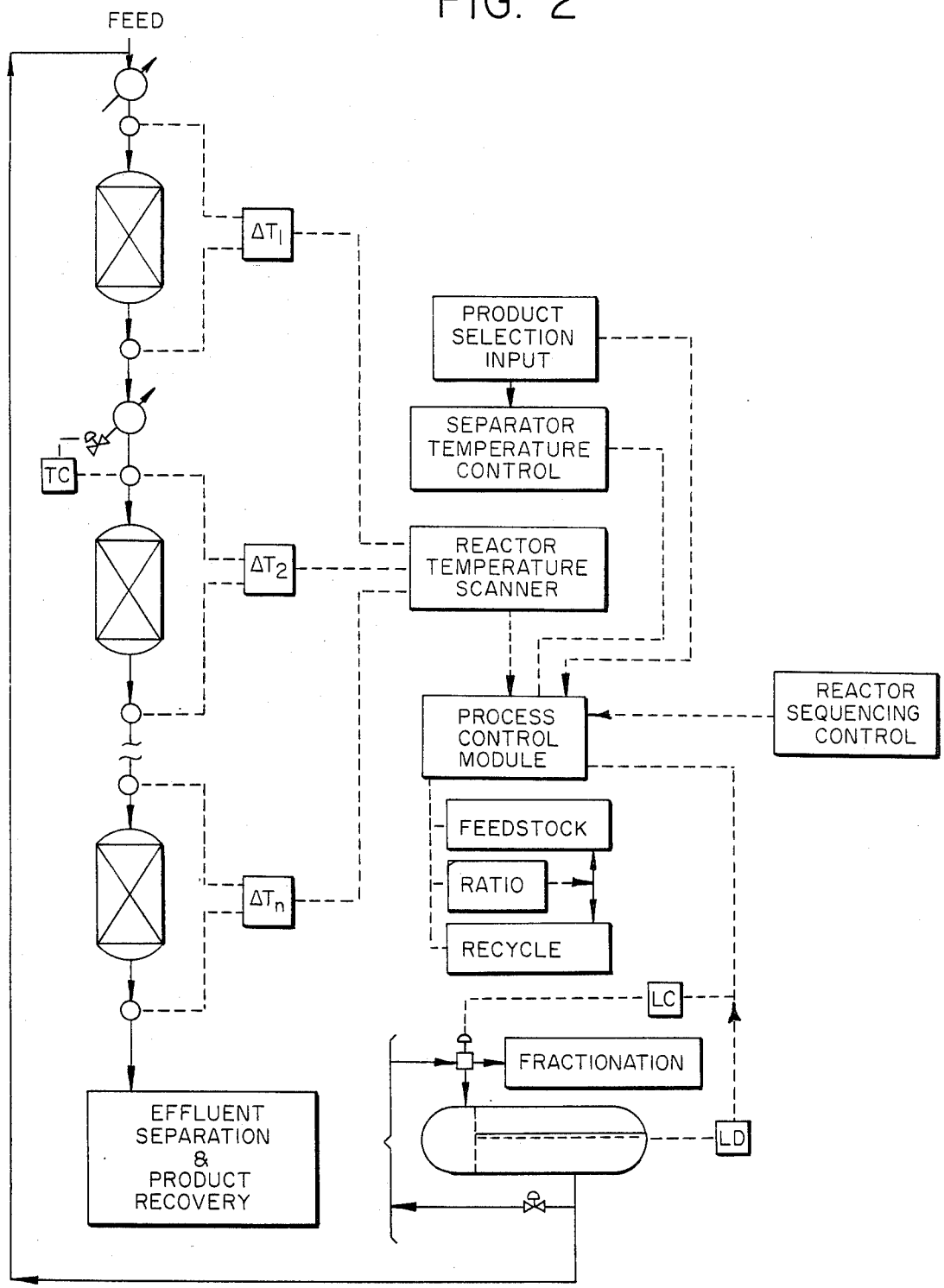
FIG. 2 is a schematic representation of a process measurement and control system, showing functional relationships between reactor and product separation components.

A distributed control system, such as a Honeywell TDC-2000, is a preferred control system module; however, equipment selection and operation mode may vary within the inventive concept. FIG. 2 depicts a typical process control diagram, showing reactor differential temperature control, effluent separation and fluid handling control functions under command of a central process control module.

Figure 3:
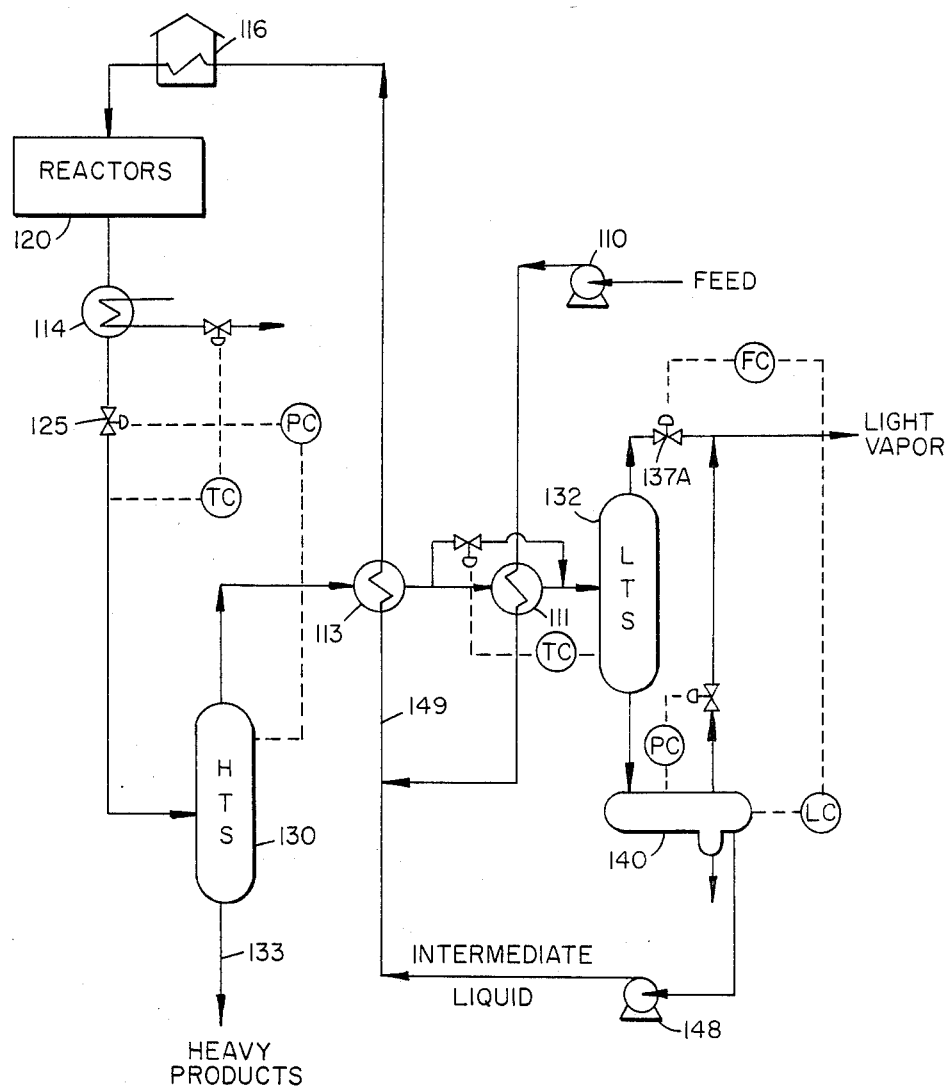
FIG. 3 is an alternative system.

In the alternative embodiment shown in FIG. 3, the control technique is applied to an effluent separation and recycle system having serial phase separators. Olefinic feed is pressurized by pump 110 and preheated in heat exchanger 111, where it partially condenses an intermediate vapor. Feed and recycle streams are combined in conduit 149 and further heated in exchanger 113, furnace 116 and contacted with conversion catalyst in reactor system 120. The reactor effluent stream is cooled in heat exchanger 114, under temperature control TC. The effluent pressure is reduced by control valve 125 under pressure control PC operatively connected to high temperature separator (HTS) 130 from which a heavy product stream may be recovered for further fractionation and finishing. An overhead vapor stream rich in intermediate and light hydrocarbons is partially condensed by passing through exchangers 113 and 111 and passed into a low temperature separator (LTS) 132, the temperature of which can be maintained by temperature controller TC and a bypass line around exchanger 111. Condensed liquid rich in intermediate range (e.g., $C_5$ to $C_9$) olefins is accumulated in surge drum 140 at a liquid level controlled by detector/controller LC operatively connected to overhead vapor valve 137A via flow controller FC. Vapor may be vented from drum 140 by a pressure controller PC. In response to the recycle flow control subsystem, the recycle stream is passed through pump 148 to conduit 149.

The high temperature separator typically operates within a temperature range of 175° to 350° C. The specific temperature depends on the desired endpoint of the recycle stream. The operating pressure may vary from 1000 to 2000 kPa(g). For example, with a typical feedstock containing 88 mol percent olefins, the separator can operate at about 220° C. and 1250 kPa(g) to obtain a 165° C. end point gasoline recycle stream.

The composition and ratio of the recycle stream are the major factors in determining the composition of the gasoline and distillate streams and, also, the ratio of gasoline to distillate product. Reactor operating pressures may vary from 2700 to 10,350 kPa(g), with a preferred pressure of about 4100 to 7000 kPa(g).

As compared to single pass operation of the process, Table I indicates the increase in distillate yield that is obtained by recycling gasoline.

TABLE I

| Comparison of Distillate Yield for Single Pass vs Gasoline Recycle | | | |
|---|---|---|---|
| | | Product Yields - Wt % | |
| Feed | | Single Pass | With Recycle |
| $C_2$ to $C_5$ with | $C_4$- | 6 | 3 |

TABLE I-continued

Comparison of Distillate Yield for Single Pass vs Gasoline Recycle

Product Yields - Wt %

| Feed | | Single Pass | With Recycle |
|---|---|---|---|
| 60 vol % C$_3$/C$_4$ | C$_5$ - 165° C. Gasoline | 27 | 18 |
| | 165°+ C. Distillate | 67 | 79 |

The effect of increasing the boiling range of the recycle stream is shown in Table II. At both 4140 kPa(g) and 5520 kPa(g) reactor inlet pressures, distillate composition becomes heavier as the boiling range and endpoint of the recycle is increased. When a heavy stream of 315° C. endpoint is recycled, a very heavy distillate or diesel fuel is obtained to increase distillate yields. Reactor pressures are increased when heavier hydrocarbon recycle streams are used.

TABLE II

Effect of Recycle Composition on Distillate Product Boiling Range

| Gasoline Recycle Ratio Mol Recycle /Mol Olefin in Fresh Feed | Reactor Inlet Pressure- kPa (g) | Gasoline Recycle End Point °C | Product Distillate Boiling Range Fraction, °C | | |
|---|---|---|---|---|---|
| | | | 5% | 50% | 95% |
| 0.5 | 4140 | 150 | 171 | 210 | 315 |
| 1.0 | 4140 | 165 | 190 | 221 | 332 |
| 2.0 | 5520 | 210 | 210 | 232 | 338 |
| 2.0 | 5520 | 232 | 221 | 265 | 354 |
| 2.0 | 10350 | 315 | 249 | 315 | 393 |

An example of gasoline and distillate production from an olefin rich stream with recycle is shown in Tables III and IV.

TABLE III

Recycle Circuit Typical Operating Conditions for Production of Gasoline and Distillate

| | |
|---|---|
| Fresh Feed - M$^3$/hr | 96.64 |
| | (14,589 BPSD) |
| Recycle Rate - M$^3$/hr | 138.11 |
| | (20,849 BPSD) |
| Recycle Ratio - Mols Recycle/Mols Feed | 1.37 |
| Separator Overhead Split, Wt Ratio | 12.9 |
| 1st Reactor Average Inlet Temperature - °C. | 302 |
| 1st Reactor Inlet Pressure - kPa (g) | 5520 |
| High Temperature Separator Temperature -°C. | 220 |
| High Temperature Separator Pressure - kPa (g) | 1240 |

TABLE IV

Feed, Recycle and Typical Product Properties[1]

| | Fresh Feed | Recycle | Gasoline | Distillate |
|---|---|---|---|---|
| M$^3$/hr | 96.64 | 138.11 | 26.27 | 53.58 |
| Spec Gravity at 15.6° C. | 0.660 | 0.659 | 0.682 | 0.797 |
| Mol Wt | 76.29 | 79.68 | 89.15 | 198.20 |
| Componential Flowrate, kg mols/hr | | | | |
| Ethene | 0.00 | 33.05 | 0.0 | 0.0 |
| Propene | 0.49 | 37.84 | 0.01 | 0.0 |
| Propane | 0.00 | 35.21 | 0.02 | 0.0 |
| Cis-2-Butene | 70.52 | 105.47 | 4.79 | 0.0 |
| Iso Butane | 6.47 | 84.06 | 0.99 | 0.0 |
| N—Butane | 6.47 | 78.75 | 2.54 | 0.0 |
| 1-Pentene | 311.89 | 95.45 | 19.46 | 0.0 |
| Iso Pentane | 26.37 | 137.24 | 27.54 | 0.0 |
| N—Pentane | 26.37 | 124.21 | 26.60 | 0.0 |
| 52-154° C. Gasoline | 386.22 | 319.19 | 114.73 | 4.92 |
| 154° C. + Distillate | 0.00 | 87.86 | 4.01 | 210.06 |
| Total kg mols/hr | 834.79 | 1137.32 | 200.67 | 214.98 |

[1] In addition, 4.61 M$^3$ hr (696 BPSD) of C$_3$/C$_4$ LPG is produced. The product volume is reduced due to differences in feed and product densities.

The temperature differential detection technique may employ individual thermal measurements with means for determining arithmetic difference between discrete values, or a differential thermocouple or the like can be employed to generate a signal representative of the inlet-outlet differential. The thermal differential signal is compared to a predetermined value. This set value may be the same for all reactors in a uniform series, or each reactor may have its maximum differential. A scanning comparator can be employed to sample each reactor temperature measurement periodically. Upon detecting a thermal excursion, the control system will alter the recycle feedstock ratio to provide a greater proportion of heat sink into the feedstream to the reactors.

It is preferred to increase recycle incrementally with increasing thermal differential until the temperature excursion is curtailed and the process restored to steady state operation under the desired conditions.

Various modifications can be made to the system, especially in the choice of equipment and non-critical processing steps. While the invention has been described by specific examples, there is no intent to limit the inventive concept as set forth in the following claims.

What is claimed is:

1. In a continuous catalytic conversion system for oligomerizing olefinic feedstock in contact with a bed of oligomerization catalyst at elevated temperature and pressure in an enclosed reaction system to produce an effluent stream comprising a mixture of heavy hydrocarbons and lighter hydrocarbons including means for flashing and phase separation of a liquid product stream rich in heavy hydrocarbons and a vapor stream rich in lighter hydrocarbons; the improvement which comprises a recycle control system including condenser means for condensing a major amount of said flashed vapor stream rich in lighter hydrocarbons, a surge drum for receiving said condensed stream, fluid handling means operatively connected between said surge drum and reactor for repressurizing and combining a predetermined amount of recycled hydrocarbons with olefinic feedstock, valve means for withdrawing a vapor slipstream between said flashing means and said condenser means to divert flashed vapors;

means for detecting liquid level of condensed hydrocarbons in said surge drum and generating a signal representative of said liquid level; and control means responsive to said level signal and operatively connected with the slipstream diverting valve means, whereby vapor slipstream flow is increased with increased surge drum liquid level above a predetermined level.

2. The conversion system of claim 1 wherein said surge drum comprises a horizontal pressure vessel having a condensed vapor inlet at one end thereof and a condensed liquid hydrocarbon outlet at an opposite end thereof, coalescer means mounted transversely in said drum for separating condensed water from condensed liquid hydrocarbon, and lower water collector boot means for withdrawing water from the system.

3. The conversion system of claim 1 wherein said reactor system comprises a series of fixed bed abiabatic zeolite catalyst zones operatively interconnected with inter zone cooling means to remove reaction exothermic heat, means for measuring reactor inlet stream and reactor outlet stream temperatures and generating a signal representative of temperature differential for each of said zones, control means responsive to said temperature measuring means for controlling temperature differential if said differential exceeds a predetermined amount for any of said catalyst zones, including recycle feedstock flow ratio control means for increasing recycle ratio in response to excess temperature differential.

4. In a continuous process for converting a feedstock mixture comprising a major amount of light olefins to higher hydrocarbons comprising distillate product wherein olefinic feedstock is combined with a pressurized liquid diluent stream comprising a major fraction of $C_5+$ olefins, and the diluted feedstock is contacted with oligomerization catalyst under exothermic reaction conditions at elevated temperature in a pressurized reactor zone to convert olefins to heavier hydrocarbons, and wherein effluent from the reactor zone is separated by reducing pressure to flash volatile components into a vapor phase to recover a heavy liquid stream from a phase separator; the improvement which comprises controlling condensation of a major portion of the vapor phase by cooling under pressure and accumulating condensate in a recycle surge vessel to provide substantially all of a liquid olefinic recycle stream for combining with the feedstock by diverting a minor portion of said vapor phase in response to liquid level in the surge vessel.

5. The process of claim 4 wherein the feedstock is combined with the olefinic recycle stream in a ratio of at least about 1 mole of recycle per mole of feedstock olefin and contacted with a fixed bed of acid aluminosilicate zeolite catalyst having a constraint index of about 1 to 12 at a reaction temperature of about 230° C. to 325° C. at process pressure of about 4000 to 7000 kPa to convert a major amount of feedstock olefins.

6. The process of claim 4 wherein composition of the heavy liquid stream from the separator is controlled by maintaining the reactor effluent at predetermined temperature prior to flashing.

7. A continuous catalytic olefin upgrading system comprising a series of fixed bed adiabatic zeolite catalyst zones operatively interconnected wth interzone cooling means to remove reaction exothermic heat; means for measuring reactor inlet stream and reactor outlet stream temperature and generating a signal representative of temperature differential for each of said zones;

control means responsive to said temperature measuring means for controlling temperature differential if said differential exceeds a predetermined amount for any of said catalyst zones;

recycle and feedstock flow ratio control means for increasing recycle ratio in response to excess temperature differential;

effluent separation means for recovering a heavy hydrocarbon product stream, intermediate liquid hydrocarbon stream and a hydrocarbon vapor stream;

surge drum means for accumulating separated intermediate range liquid hydrocarbon, said surge drum means being operatively connected to a condenser means, separator overhead vapor diverter valve means, and recycle conduit means;

liquid level detector means for generating a signal representative of liquid level in said surge drum; and liquid level control means operatively connected to divert overhead vapor from said condenser means in response to increased liquid level in said surge drum.

* * * * *